(12) United States Patent
Jan et al.

(10) Patent No.: US 6,465,641 B1
(45) Date of Patent: Oct. 15, 2002

(54) ONE POT SYNTHESIS OF 5'-HYDROXY PHOSPHORYLATED NUCLEOSIDE DERIVATIVES, AND COMPOUNDS FORMED THEREBY

(75) Inventors: Shyi-Tai Jan, Roseville; Fatih M. Uckun, White Bear Lake, both of MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/957,365

(22) Filed: Sep. 19, 2001

Related U.S. Application Data

(63) Continuation of application No. PCT/US00/07193, filed on Mar. 17, 2000.
(60) Provisional application No. 60/125,137, filed on Mar. 19, 1999.

(51) Int. Cl.$^7$ ................................................ C07H 19/04
(52) U.S. Cl. .................... 536/26.1; 536/22.1; 536/18.7; 536/55.3; 536/124
(58) Field of Search ............................... 536/17.1, 17.2, 536/18.4, 18.6, 26.1, 55, 55.3

(56) References Cited

U.S. PATENT DOCUMENTS

| | | | |
|---|---|---|---|
| 6,030,957 A | * | 2/2000 | Uckun et al. .................. 514/51 |
| 6,191,120 B1 | * | 2/2001 | D'Cruz et al. ................. 514/50 |
| 6,350,736 B1 | * | 2/2002 | Uckun et al. .................. 514/51 |
| 2002/0022600 A1 | * | 2/2002 | D'Cruz et al. ................. 514/50 |
| 2002/0025922 A1 | * | 2/2002 | D'Cruz et al. ................. 514/7 |

FOREIGN PATENT DOCUMENTS

| | | |
|---|---|---|
| WO | WO 93 23416 | 11/1993 |

* cited by examiner

*Primary Examiner*—James O. Wilson
*Assistant Examiner*—Patrick Lewis
(74) *Attorney, Agent, or Firm*—Merchant & Gould P.C.

(57) ABSTRACT

A method for the preparation of 5'-hydroxy phosphorylated nucleoside derivatives in a single reaction vessel is provided. The method includes contacting phosphorous oxychloride with a halophenyl moiety followed by contacting the resulting halophenylphosphorodichloridate with a carboxy-protected amino acid and finally contacting the resulting halophenyl carboxy-protected amino acid phosphorochloridate with a nucleoside.

20 Claims, No Drawings

ONE POT SYNTHESIS OF 5'-HYDROXY PHOSPHORYLATED NUCLEOSIDE DERIVATIVES, AND COMPOUNDS FORMED THEREBY

PRIORITY OF THE INVENTION

This application is a continuation application of international application number PCT/US00/07193 filed on Mar. 17, 2000 claiming priority under 35 U.S.C. 119 (a)–(e) to U.S. Provisional Application No. 60/125,137 filed on Mar. 19, 1999; the international application was published under PCT Article 21(2) in English as WO 00/56750.

FIELD OF THE INVENTION

This invention relates to a one pot synthetic method for the synthesis of 5'-hydroxy phosphorylated nucleoside derivatives.

BACKGROUND OF THE INVENTION

The spread of AIDS and the ongoing efforts to control the responsible virus are well-documented. One way to control HIV is to inhibit its reverse transcriptase activity (RT). Thus, novel, potent, and selective inhibitors of HIV RT are needed as useful therapeutic agents. Known, potent inhibitors of HIV RT include 5'-triphosphates of 2',3'-dideoxynucleoside ("ddN") analogues. Various 5'-hydroxy phosphorylated 2',3'-dideoxynucleoside derivatives such as phenyl phosphate derivatives of 3'-azidothymidine (AZT), 2',3'-didehydro-2',3'-dideoxythymidine (d4T) and 3'-deoxythymidine (3dT) have long been tested as anti-HIV agents. Given the significance of ddN derivatives, development of new methodologies for their synthesis, especially syntheses amenable to large scale commercial production and affording a high yields, is important.

Despite intensive research regarding the preparation of ddN derivatives, the synthesis of 5'-hydroxy phosphorylated ddN derivatives has involved synthetic methodology requiring at least three separate synthetic steps each usually involving purification of the resulting intermediate. The most commonly used synthetic procedure affording 5'-hydroxy phosphorylated ddN derivatives is the three-step synthetic sequence shown in Scheme 1.

Scheme 1

STEP 1

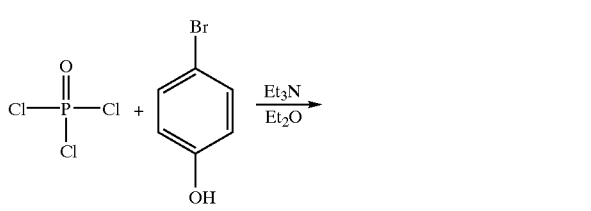

STEP 2

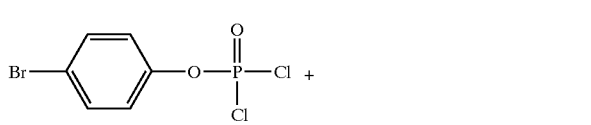

-continued

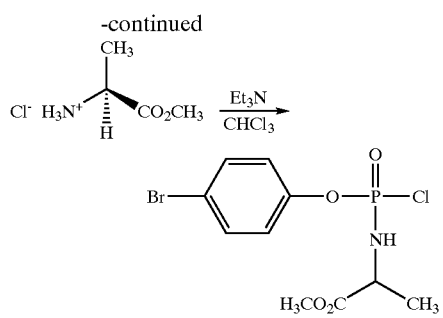

STEP 3

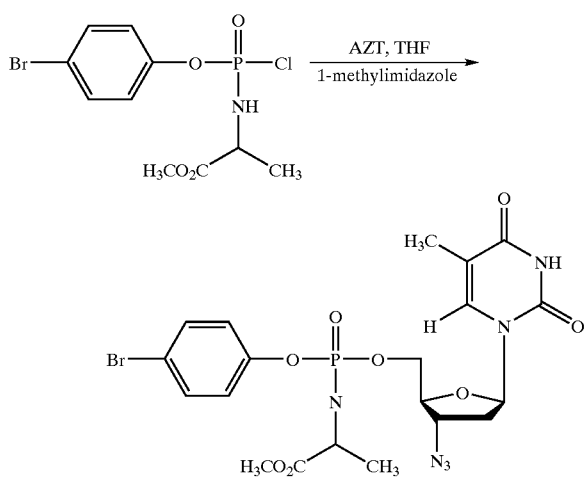

The current methods for the synthesis of 5'-hydroxy phosphorylated ddN derivatives suffer from a variety of disadvantages. For example, the commonly used synthetic method of Scheme 1 involves multiple solvents and a variety of work up and purification procedures. Specifically, the method of Scheme 1 uses three different solvents for the three separate steps, namely $Et_2O$ in the first step, $CHCl_3$ in the second step and THF in the third step. Additionally, the method of Scheme 1 requires purification of the p-bromophenyl phosphorodichloridate intermediate via distillati In at the end of step 1 and removal of HCl amine salts formed at the end of step 2. The use of these additional work up, and purification steps, as well as multiple reagents increases the production costs and decreases the yields of 5'-hydroxy phosphorylated ddN derivatives. Furthermore, existing synthetic methods for production of 5'-hydroxy phosphorylated ddN derivatives are not amenable to large scale commercial production.

SUMMARY OF THE INVENTION

Generally, the present invention relates to a method for preparing a 5'-hydroxy phosphorylated nucleoside compound in a single reaction vessel. The method provides a high yielding synthesis of 5'-hydroxy phosphorylated nucleoside compounds and related derivatives without the need for purification and isolation of intermediates, and is amenable to large scale synthesis.

The invention provides a method for preparing a 5'-hydroxy phosphorylated nucleoside compound in a single reaction vessel. Phosphorous oxychloride is contacted with a halophenol moiety to produce a halophenyl phosphorodichloridate. Without purification, the halophenyl phosphorodichloridate is reacted with a carboxy-protected amino acid to produce a halophenyl carboxy-protected amino acid phosphorochloridate. Without purification, the halophenyl carboxy-protected amino acid phosphorochloridate is reacted with a nucleoside.

One embodiment of the invention provides a method of preparing AZT-5'-(para-bromophenyl methoxyalaninyl phosphate) in a single reaction vessel without purification of the intermnediates formed. Phosphorous oxychloride is reacted with a para-bromophenol moiety to form para-bromophenyl phosphorodichloridate. Without purification, the para-bromophenyl phosphorodichloridate is contacted with alanine methyl ester to produce para-bromophenyl methoxyalaninyl phosphorochloridate. Without purification, the para-bromophenyl methoxyalaninyl phosphorochloridate is reacted with AZT.

Another embodiment of the invention provides a method of preparing d4T-5'-(para-bromophenyl methoxyalaninyl phosphate) in a single reaction vessel without purification of the intermediates formed. Phosphorous oxychloride is reacted with a para-bromophenol moiety to form para-bromophenyl phosphorodichloridate. Without purification, the para-bromophenyl phosphorodichloridate is contacted with alanine methyl ester to produce para-bromophenyl methoxyalaninyl phosphorochloridate. Without purification, the para-bromophenyl methoxyalaninyl phosphorochloridate is reacted with d4T.

DETAILED DESCRIPTION OF THE PREFERRED EMBODIMENT

The present invention is applicable to the preparation of 5'-hydroxy phosphorylated nucleoside derivatives. In particular, the present invention is directed to a method for the synthesis of 5'-hydroxy phosphorylated nucleoside derivatives in a single reaction vessel without the need for purification or isolation of reaction intermediates. While the present invention is not so limited, an appreciation of various aspects of the invention will be gained through a discussion of the examples provided below.

The method involves the synthesis of 5'-hydroxy phosphorylated nucleoside derivatives in a single reaction vessel by the sequential addition of various reagents. Synthesis of 5'-hydroxy phosphorylated 2',3'-dideoxynucleoside derivatives is carried out in a single reaction vessel. Phosphorous oxychloride is contacted with a halophenol moiety to produce a halophenylphosphorodichloridate. Without purification, the halophenyl phosphorochloridate is reacted with a carboxy-protected amino acid to produce a halophenyl carboxy-protected amino acid phosphorochloridate. Without purification, the halophenyl carboxy-protected amino acid phosphorochloridate is reacted with a nucleoside.

First, a halophenyl phosphorodichloridate species is formed by contacting phosphorous oxychloride with a halophenol moiety in the presence of an organic solvent and a tertiary amine. Suitable halophenol moieties include a phenyl group substituted with 1 to 5 halogens selected from fluorine, chlorine, bromine, iodine, or a mixture thereof. Preferred halophenol moieties include para-halogenated phenol moieties. A most preferred halophenol moiety is a para-bromo phenol moiety.

The phosphorous oxychloride and halophenol moiety are typically contacted in an organic solvent which is suitable for every chemical transformation involved in synthesizing 5'-hydroxy phosphorylated 2',3'-dideoxynucleoside derivatives in a single reaction vessel. Examples of suitable organic solvents include ethers, such as diethyl ether ($Et_2O$), chlorinated solvents, such as methylene chloride ($CH_2Cl_2$), chloroform, or dichloroethane, and aromatics, such as toluene, or tetrahydrofurane (THF). Preferably, the organic solvent is THF or methylene chloride. The phosphorous oxychloride and halophenol moiety are typically contacted in the presence of a tertiary amine. Examples of tertiary amines include triethylamine ($Et_3N$), 1-methylimidazole, trimethylamine, tri-n-propylamine, N,N-dimethylaniline, and triphenylamine. Preferably, the tertiary amine is triethylamine or 1-methylimidazole. Most preferably the tertiary amine is triethylamine.

The present method typically employs a molar ratio of $POCl_3$ to the halophenol moiety of about 0.5:1 to about 1:3. Preferably, the molar ratio of $POCl_3$ to the halophenol moiety is equal or a slight molar excess of the halophenol moiety is employed. Preferably, the molar ratio of $POCl_3$ to the halophenol moiety is from about 1:1 to about 1:2. Most preferably, a $POCl_3$ to halophenol moiety ratio of about 1:1 to about 1:1.2 is employed. Additionally, the molar ratio of tertiary amine to halophenol moiety is from about 0.5:1 to about 3:1. Preferably, the molar ratio of tertiary amine to halophenol moiety is from about 1:1 to about 2:1. Most preferably, the molar ratio of tertiary amine to halophenol moiety is from about 1:1 to about 1.2:1.

The reaction time necessary to form the halophenyl phosphorodichloridate species will depend on temperature, stoichiometric ratios of the reagents, and the halophenol reagent utilized. Generally, reaction times range from about 1 to 20 hours. Typically, reaction times range from about 12 to about 15 hours.

In the presence of a tertiary amine, the phosphorous oxychloride ($POCl_3$) and halophenol moiety are initially contacted at about 0° C. The resulting reaction mixture is preferably maintained at a temperature of about 25° C. Temperatures of about −20° C. to about 30° C. are employed in order to maintain a convenient reaction rate without substantially decreasing yield.

A halophenyl carboxy-protected amino acid phosphorochloridate moiety is then formed by contacting the halophenyl phosphorodichloridate formed above with a carboxy-protected amino acid in the same reaction vessel. The carboxy-protected amino acid and the halophenyl phosphorodichloridate formed above are contacted in the presence of an organic solvent and a tertiary amine as defined above.

Carboxy-protected amino acids can be prepared from a natural or synthetic amino acid and a carboxy-protecting group using methods known to those skilled in the art. Typical methods for preparing carboxy-protected amino acids include, for example, the preparation of the methyl ester, ethyl ester, benzyl ester, methoxymethyl ester, and benzyloxymethyl ester. Suitable carboxy protective groups and methods for the preparation of carboxy-protected amino acids are described in *Protective Groups in Organic Synthesis,* Greene, ed., John Wiley & Sons, New York (1981) and *The Peptides: Analysis, Synthesis, Biology: Vol.3: Protections of Functional Groups in Peptide Synthesis,* E. Gross and J. Meinenhofer, eds., Academic Press, New York (1981), the disclosures of which are incorporated herein by reference.

Suitable carboxy-protected amino acids include carboxy-protected natural and synthetic amino acids. "Amino acid" refers to any of the naturally occurring amino acids, as well as optical isomers (enantiomers and diastereomers), synthetic analogs and derivatives thereof. α-Amino acids include a carbon atom to which is bonded an amino group, a carbonyl group, a hydrogen atom, and a distinctive side chain. The side chains of naturally occurring amino acids are well known in the art and include, for example, hydrogen (e.g., as in glycine), alkyl (e.g. as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroalkyl (e.g., as in histidine). One of skill in the art will appreciate that the term amino acid also includes β-, γ-, δ-, and ω-amino acids, and the like. Synthetic amino acids such as, for example, alanine, glycine, valine, phenylalanine, cysteine, serine, lysine, glutamate, glutamine, trifluoroleucine, p-fluorophenylalanine, and 3-triethylalanine are also known in the art. Typically, the carboxy protected amino acids are esters of natural and synthetic amino acids. Preferably, the carboxy protected amino acid is an alanine ester. Most preferably the carboxy protected amino acid is alanine methyl ester.

The present method typically employs a molar ratio of carboxy-protected amino acid to POCl$_3$ of about 0.5:1 to about 3:1. Preferably, the molar ratio of carboxy-protected amino acid to POCl$_3$ is equal or a slight molar excess of the carboxy-protected amino acid is employed. Preferably, the molar ratio of carboxy-protected amino acid to POCl$_3$ is from about 1:1 to about 2:1. Most preferably, a carboxy-protected amino acid to POCl$_3$ molar ratio of about 1:1 to about 1.2:1 is employed. An additional amount of triethylamine is added to the reaction vessel subsequent to the addition of the carboxy-protected amino acid. This second portion of triethylamine is added at a molar ratio from about 0.5:1 to about 4:1, triethylamine to carboxy-protected amino acid. Preferably, the molar ratio of tertiary amine to carboxy-protected amino acid is from about 1:1 to about 2:1. Most preferably, the molar ratio of tertiary amine to carboxy-protected amino acid is from about 1:1 to about 2:1.

The reaction time necessary to form the halophenyl carboxy-protected amino acid phosphorochloridate species will depend on temperature, stoichiometric ratios of the reagents, and the halophenyl phosphorodichloridate reagent utilized. Generally, reaction times range from about 1 to 20 hours. Typically, reaction times range from about 12 to about 15 hours.

When forming the halophenyl carboxy-protected amino acid phosphorochloridate species temperatures of about −70° C. to about 30° C. are preferably employed in order to maintain a convenient reaction rate without substantially decreasing yield.

Finally, the desired 5'-hydroxy phosphorylated 2',3'-dideoxynucleoside derivative is formed by contacting a halophenyl carboxy-protected amino acid phosphorochloridate formed above with the desired 2',3'-dideoxynucleoside in the same reaction vessel. The halophenyl carboxy-protected amino acid phosphorochloridate and the desired 2',3'-dideoxynucleoside are contacted in the presence of an organic solvent and a tertiary amine as defined above.

The present method typically employs a molar ratio of 2',3'-dideoxynucleoside to POCl$_3$ of about 0.25:1 to about 2:1. Preferably, the molar ratio of 2',3'-dideoxynucleoside to POCl$_3$ is from about 0.33:1 to about 1:1.2. Most preferably, the molar ratio of 2',3'-dideoxynucleoside to POCl$_3$ is from about 1:1 to about 1:1.2. An additional amount of triethylamine is added to the reaction vessel either subsequent to or concurrent with the addition of the 2',3'-dideoxynucleoside. This third portion of triethylamine is added at a molar ratio from about 0.25:1 to about 7:1 triethylamine to POCl$_3$. Preferably, the molar ratio of tertiary amine to POCl$_3$ is from about 0.33:1 to about 6:1. Most preferably, the molar ratio of tertiary amine to POCl$_3$ is from about 1:1 to about 6:1.

The reaction time necessary to form desired 5'-hydroxy phosphorylaed 2',3'-dideoxynucleoside derivative will depend on temperature, stoichiometric ratios of the reagents, and the halophenyl carboxy-protected amino acid phosphorochloridate and 2',3'-dideoxynucleoside reagents utilized. Generally, reaction times range from about 10 to 50 hours. Typically, reaction times range from about 24 to about 48 hours.

The halophenyl carboxy-protected amino acid phosphorochloridate and 2',3'-dideoxynucleoside are initially contacted at about 20° C. to 30° C. The resulting reaction mixture is maintained at a temperature of about 20° C. to 30° C. Temperatures of about 0° C. to about 30° C. are typically employed in order to maintain a convenient reaction rate without substantially decreasing yield.

As used herein the term "halophenol moiety," unless stated otherwise, refers to a phenol group substituted with 1 to 5 halogens.

As used herein the term "halogen," unless stated otherwise, refers to fluorine, chlorine, bromine, or iodine.

As used herein the term "amino acid" unless stated otherwise, refers to α and β amino derivatives of aliphatic carboxcyclic acids. The term "amino acids" includes both natural and synthetic amino acids such as, for example, alanine, glycine, valine, phenylalanine, cysteine, serine, lysine, glutamate, glutamine, trifluoroleucine, p-fluorophenylalanine, and 3-triethylalanine.

As used herein the term "nucleoside," unless stated otherwise, refers to any glycoside that is a component of a nucleic acid and that consists of a nitrogenous base linked to a ribofuranose such as, for example, 2',3'-dideoxynucleosides. Typically, nucleosides include those substituted at the 1' position. Preferably, the substituent at the 1' position is purine or pyrimidine. Most preferably the substituent at the 1' position is thymine. Suitable nucleosides include those having the following formulae:

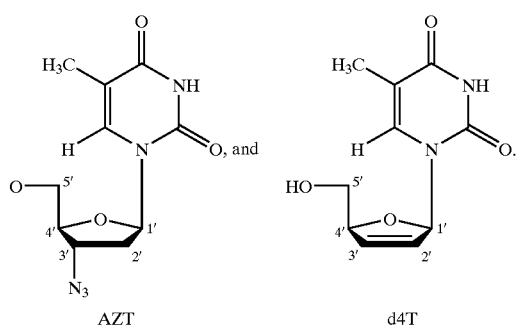

One embodiment of the invention provides a method of preparing AZT-5'-(para-bromophenyl methoxyalaninyl phosphate) as shown in Scheme 2. The AZT-5'-(para-bromophenyl methoxyalaninyl phosphate) is prepared in a single reaction vessel without purification of the intermediates.

Scheme 2

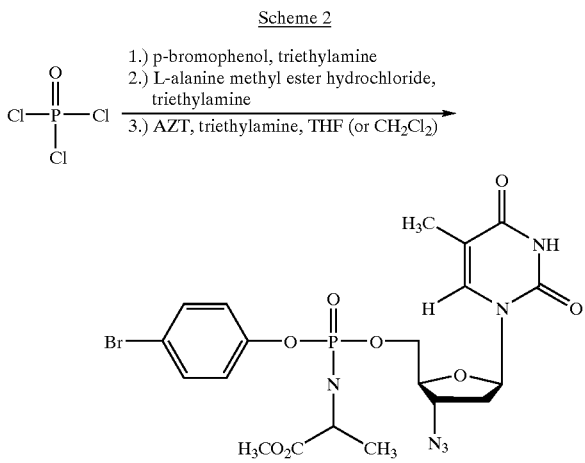

Phosphorous oxychloride is reacted with a para-bromophenol moiety to form para-bromophenyl phosphorodichloridate. Without purification, the para-bromophenyl phosphorodichloridate is contacted with alanine methyl ester to produce para-bromophenyl methoxyalaninyl phosphorochloridate. Without purification, the para-bromophenyl methoxyalaninyl phosphorochloridate is reacted with AZT.

Another embodiment of the invention provides a method of preparing d4T-5'-(para-bromophenyl methoxyalaninyl phosphate) in a single reaction vessel without purification of the intermediates formed. Phosphorous oxychloride is reacted with a para-bromophenol moiety to form para-bromophenyl phosphorodichloridate. Without purification, the para-bromophenyl phosphorodichloridate is contacted with alanine methyl ester to produce para-bromophenyl methoxyalaninyl phosphorochloridate. Without purification, the para-bromophenyl methoxyalaninyl phosphorodichloridate is reacted with d4T.

The products formed using the methods of the invention can be used to form other chemical compounds. In one embodiment, the 5'-hydroxy phosphorylated nucleoside can be treated with a solution of bromine in methanol to produce, for example, a 5-bromo-6-methoxy-5,6-dihydro-AZT-5'-(halophenyl carboxy-protected amino acid phosphate) or 5-bromo-6-methoxy-5,6-dihydro-d4T-5'-(halophenyl carboxy-protected amino acid phosphate). Such molecules have demonstrated combined spermicidal and anti-HIV activity. For example, 5-bromo-6-methoxy-5,6-dihydro-AZT-5'-(p-bromophenyl methoxyalaninyl phosphate) has demonstrated an $EC_{50}$ value of 2.8 $\mu$M in sperm motility assays and an $IC_{50}$ value of 0.005 $\mu$M in HIV replication assays.

EXAMPLES

Example 1

Synthesis of AZT-5'-p-bromophenyl methoxyalaninyl phosphate)

A solution of p-bromophenol (7.2 g, 42 mmol) and triethylamine (5.7 mL, 42 mmol) in anhydrous methylene chloride (135 mL) was added dropwise to a stirred solution of $POCl_3$ (3.9 mL, 42 mmol) in anhydrous methylene chloride (105 mL) at 0° C. under a nitrogen atmosphere over a period of 1 hour. The reaction was allowed to warm to room temperature and stirred for 15 hours. An aliquot was taken from the reaction, dried and analyzed by $^1$H NMR. $^1$H NMR spectrum of the aliquot showed the formation of p-bromophenyl phosphorodichloridate. A solution of L-alanine methyl ester hydrochloride (5.85 g, 42 mmol) in anhydrous $CH_2Cl_2$ (90 mL) was added to the reaction flask at room temperature. The reaction mixture was then cooled to −70° C. followed by the dropwise addition of triethylamine (11.7 mL, 84 mmol) in anhydrous methylene chloride (120 mL) over 45 minutes. After the addition of the triethylamine solution, the reaction mixture was allowed to warm to room temperature and stirred overnight. An aliquot was taken from the reaction and dried. The $^1$H NMR spectrum of the aliquot showed the formation of p-bromophenyl methoxyalaninylphosphorochloridate; While under a positive atmosphere of nitrogen AZT (11.3 g, 42 mmol) was added to above reaction flask as a solid. Neat triethylamine (35.1 mL, 252 mmol) was then added to the reaction mixture at room temperature. The reaction solution was stirred in the dark under an inert nitrogen atmosphere for 2 days. An aliquot was taken from the reaction, dried, and analyzed by $^1$H NMR and TLC (co-spotting with an authentic sample of the desired product). After confirming the formation of the desired product, the stirring was stopped and the solvent was removed by a rotary evaporator. The crude product was purified by column chromatography (silica gel 230–400 mesh; eluant: 100% $CHCl_3$ followed by 2% MeOH in $CHCl_3$) to yield 10.6 grams (43% overall yield) of AZT-5'-(p-bromophenyl methoxyalaninyl phosphate) as a white solid. IR (KBr) 3206, 3066, 2955, 2110, 1745, 1691, 1485, 1271, 1153, 1011, 926 cm$^{-1}$; $^1$H NMR (300 MHz, $CDCl_3$) δ8.69 (1H, br, 3-NH), 7.45 (2H, d, J=9.0 Hz, aryl H), 7.34 & 7.32 (1H, s & s, vinyl H), 7.11 (2H, d, J=9.0 Hz, aryl H), 6.18 & 6.13 (1H, t & t, J=6.6 & 6.6Hz, H at C-1'), 4.44–3.77 (6H, m, H at C-3',4'& 5', Ala—NH and Ala—CH), 3.73 & 3.72 (3H, s & s, —COOCH$_3$), 2.51–2.20 (2H, m, H at C-2'), 2.18 (3H, s, —CH$_3$ at C-5), 1.39 & 1.36 (3H, d & d, Ala—CH$_3$). $^{13}$C NMR (75 MHz, $CDCl_3$) δ173.6, 163.6, 150.1, 149.2, 149.1, 135.2, 132.4, 121.6, 117.8, 111.1, 85.0, 84.7, 81.9, 81.8, 65.5, 60.1, 59.9, 52.4, 50.0, 49.9, 36.9, 20.6, 20.5, 12.2; $^{31}$P NMR ($CDCl_3$) δ2.88, 2.62; MS (CI, m/e) 589.1 (M$^+$, $^{81}$Br) and 587.1 (M$^+$, $^{79}$Br).

Example 2

Synthesis of d4T-5'-(p-bromo methoxyalaninyl phosphate)

d4T-5'-(p-bromo methoxyalaninyl phosphate) was prepared according to the same method as outlined in Example 1 except that AZT was replaced with d4T (overall yield 35%). IR (neat): 3203, 3070, 2954, 2887, 2248, 1743, 1693, 1485, 1221, 1153, 1038, 912, 835, 733 cm$^{-1}$. $^1$H NMR ($CDCl_3$) δ9.60–0.58 (br s, 1H), 7.45–7.42 (m, 2H), 7.30–7.09 (m, 4H), 6.37–6.27 (m, 1H), 5.93–5.88 (m, 1H), 5.04–5.01 (br m, 1H), 4.35–4.33 (m, 2H), 4.27–3.98 (m, 2H), 3.71–3.70 (s, 3H), 1.85–1.81 (s, 3H), 1.37–1.31 (m, 3H); $^{13}$C NMR ($CDCl_3$) δ6173.7, 163.8, 150.8, 149.7–149.6, 135.6–135.4, 133.1–132.5, 127.4–127.3, 121.9–121.7, 118.0, 111.2–111.1, 89.7–89.4, 84.4–84.3, 67.8–66.4, 52.5, 50.0–49.9, 20.7, and 12.3; $^{31}$P NMR ($CDCl_3$) δ3.41, 2.78; MALDI-TOF mass calculated (M+Na) 567.2, found 5567.1.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

The content of all publications, patents, and patent documents described and cited herein is incorporated by reference as if fully set forth. The invention described herein may be modified to include alternative embodiments. All such obvious alternatives are within the spirit and scope of the invention, as claimed below.

What is claimed is:

1. A method for preparing a 5'-hydroxy phosphorylated nucleoside compound in a single reaction vessel comprising:
   a) contacting phosphorous oxychloride with a halophenol moiety to produce a halophenyl phosphorodichloridate;
   b) without purification of said halophenylphosphorodichloridate, contacting the halophenyl phosphorodichloridate with a carboxy-protected amino acid to produce a halophenyl carboxy-protected amino acid phosphorochloridate; and
   c) without purification of said halophenyl carboxy-protected amino acid phosphorochloridate, contacting the halophenyl carboxy-protected amino acid phosphorochloridate with a nucleoside.

2. The method of claim 1, wherein the halophenol moiety comprises a phenyl group substituted with 1 to 5 halogens.

3. The method of claim 2, wherein the halogens are selected from the group consisting of fluorine, chlorine, bromine, and iodine.

4. The method of claim 1, wherein the halophenol moiety comprises a para-boromophenol moiety.

5. The method of claim 1, wherein the carboxy-protected amino acid comprises an ester of a natural or synthetic amino acid.

6. The method of claim 5, wherein the ester is selected from the group consisting of methyl ester, ethyl ester, benzyl ester, methoxymethyl ester, and benzyloxymethyl ester.

7. The method of claim 5, wherein the carboxy-protected amino acid comprises alanine methyl ester.

8. The method of claim 1, wherein the nucleoside is selected from the group consisting of AZT and d4T.

9. The method of claim 1, wherein the nucleoside comprises 2',3'-dideoxynucleoside substituted at the 1' position with a purine or pyrimidine.

10. The method of claim 1, wherein the nucleoside comprises 2',3'-dideoxynucleoside substituted at the 1' position with thymine.

11. The method of claim 1, comprising contacting the phosphorous oxychloride with a halophenol moiety, contacting the halophenyl phosphorochloridate with a carboxy-protected amino acid and contacting the halophenyl carboxy-protected amino acid phosphorochloridate with a nucleoside in the presence of an organic solvent;
    wherein the organic solvent is selected from the group consisting of ethers, chlorinated solvents, aromatics, and tetrahydrofuran.

12. The method of claim 11, wherein the organic solvent is selected from the group consisting of tetrahydrofuran and methylene chloride.

13. The method of claim 1, comprising contacting the phosphorous oxychloride with a halophenol moiety, contacting the halophenyl phosphorodichloridate with a carboxy-protected amino acid and contacting the halophenyl carboxy-protected amino acid phosphorochloridate with a nucleoside in the presence of a tertiary amine;
    wherein the tertiary amine is selected from the group consisting of triethylamine, 1-methylimidazole, trimethylamine, tri-n-propylamine, N,N-dimethylaniline, and triphenylamine.

14. The method of claim 13, wherein the tertiary amine is triethylamine.

15. The method of claim 1, wherein the molar ratio of the phosphorous oxychloride to halophenol moiety is from about 1:1 to about 1:1.2.

16. The method of claim 1, wherein the molar ratio of the carboxy-protected amino acid to phosphorous oxychloride is from about 1:1 to about 1.2:1.

17. The method of claim 1, wherein the molar ratio of nucleoside to phosphorous oxychloride is from about 1:1 to about 1:1.2.

18. The method of claim 1, wherein the molar ratio of tertiary amine to phosphorous oxychloride is from about 1:1 to about 6:1.

19. A method for preparing AZT-5'-(para-bromophenyl methoxyalaninyl phosphate) in a single reaction vessel comprising:
    a) contacting phosphorous oxychloride with a para-bromophenol moiety to form para-bromophenyl phosphorodichloridate;
    b) without purification of said para-bromophenyl phosphorodichloridate, contacting the para-bromophenyl phosphorodichloridate with alanine methyl ester to produce para-bromophenyl methoxyalaninyl phosphorochloridate; and
    c) without purification of said para-bromophenyl methoxyalaninyl phosphorochloridate, contacting the para-bromophenyl methoxyalaninyl phosphorochloridate with AZT.

20. A method for preparing d4T-5'-(para-bromophenyl methoxyalaninyl phosphate) in a single reaction vessel comprising:
    a) contacting phosphorous oxychloride with a para-bromophenol moiety to form para-bromophenyl phosphorodichloridate;
    b) without purification of said para-bromophenyl phosphorodichloridate, contacting the para-bromophenyl phosphorodichloridate with alanine methyl ester to produce para-bromophenyl methoxyalaninyl phosphorochloridate; and
    c) without purification of said para-bromophenyl methoxyalaninyl phosphorochloridate, contacting the para-bromophenyl methoxyalaninyl phosphorochloridate with d4T.

* * * * *

UNITED STATES PATENT AND TRADEMARK OFFICE
CERTIFICATE OF CORRECTION

PATENT NO. : 6,465,641 B1
DATED : October 15, 2002
INVENTOR(S) : Jan et al.

It is certified that error appears in the above-identified patent and that said Letters Patent is hereby corrected as shown below:

Title page,
Item [56], References Cited, please insert -- Venkatachalam T., et al.: "Enhancing Effects Of A Mono-Bromo Substitution At The Para Position Of The Phenyl Moiety On The Metabolism And Anti-HIV Activity Of D4T-Phenyl Methoxyalaninyl Phosphate Derivatives," *Bioorganic & Medicinal Chemistry Letters, Gb, Oxford*, Vol. 8, No. 22, pages 3121-3126 (November 17, 1998). --

Column 2,
Line 44, "via distillati" should read -- via distillation --

Column 3,
Line 7, "intermnediates" should read -- intermediates --

Column 7,
Line 59, "Synthesis of AZT-5' - p-bromophenyl" should read -- Synthesis of AZT-5' - (p-bromophenyl --

Column 8,
Line 57, "$\delta6173.7$" should read -- $\delta173.7$ --

Signed and Sealed this

Eleventh Day of March, 2003

JAMES E. ROGAN
*Director of the United States Patent and Trademark Office*